(12) United States Patent
Miglio et al.

(10) Patent No.: US 11,898,189 B2
(45) Date of Patent: Feb. 13, 2024

(54) MICROALGAL STRAIN AND ITS USE FOR THE PRODUCTION OF LIPIDS

(71) Applicant: ENI S.P.A., Rome (IT)

(72) Inventors: Roberta Miglio, Novara (IT); Tomas Morosinotto, Desenzano del Garda (IT); Alessandra Bellan, Cavarzere (IT)

(73) Assignee: ENI S.P.A., Rome (IT)

( * ) Notice: Subject to any disclaimer, the term of this patent is extended or adjusted under 35 U.S.C. 154(b) by 231 days.

(21) Appl. No.: 17/311,426

(22) PCT Filed: Dec. 5, 2019

(86) PCT No.: PCT/IB2019/060472
§ 371 (c)(1),
(2) Date: Jun. 7, 2021

(87) PCT Pub. No.: WO2020/115692
PCT Pub. Date: Jun. 11, 2020

(65) Prior Publication Data
US 2022/0025414 A1 Jan. 27, 2022

(30) Foreign Application Priority Data
Dec. 6, 2018 (IT) .................. 102018000010858

(51) Int. Cl.
*C12P 7/64* (2022.01)
*C12N 1/12* (2006.01)
*C12R 1/89* (2006.01)

(52) U.S. Cl.
CPC .................. *C12P 7/64* (2013.01); *C12N 1/12* (2013.01); *C12R 2001/89* (2021.05)

(58) Field of Classification Search
CPC .......... C12P 7/64; C12N 1/12; C12R 2001/89
See application file for complete search history.

(56) References Cited

U.S. PATENT DOCUMENTS

2014/0295448 A1   10/2014   Kirst et al.

FOREIGN PATENT DOCUMENTS

| EP | 1728844 A1 | 12/2006 |
|---|---|---|
| WO | 2014102254 A1 | 7/2014 |

OTHER PUBLICATIONS

Perin et al, "Generation of random mutants to improve light-use efficiency of Nannochloropsis gaditana cultures for biofuel production." Biotechnology for biofuels 8 (2015): 1-13 (Year: 2015).*
Atsushi Hara et al, "Lipid Extraction of Tissues with a Low-Toxicity Solvent", Analytical Biochemistry, 1978, vol. 90, pp. 420-426.
Emma L. Smith et al., "Deep Eutectic Solvents (DESs) and Their Applications", Chemical Reviews, 2014, vol. 114, pp. 11060-11082.
Giorgio Perin et al., "Cultivation in industrially relevant conditions has a strong influence on biological properties and performances of Nannochloropsis gaditana genetically modified strains", Agal Research, Dec. 1, 2017, vol. 28, p. 88-99, XP055605000.
Giorgio Perin et al. "Generation of random mutants to improve light-use efficiency of Nannochloropsis gaditana cultures for biofuel production", Biotechnology for Biofuels, Sep. 25, 2015, vol. 8, No. 161, pp. 1-13, XP055604948.
International Search Report dated Feb. 3, 2020 re: Application No. PCT/IB2019/060472, pp. 1-4, citing: Perin et al. "Generation of random mutants . . . ", Verruto et al. "Unrestrained markerless trait stacking . . . ", Perin et al. "Cultivation in industrially relevent conditions . . . ", Mooij et al. "Antenna size reduction . . . ".
John Verruto et al., "Unrestrained markerless trait stacking in Nannochloropsis gaditana through combined genome editing and marker recycling technologies", Applied Biological Sciences PNAS, vol. 115, No. 30, Jul. 9, 2018, pp. E7015-E7022, XP055604939.
Jordi Folch et al., "A Simple Method for the Isolation and Purification of Total Lipides From Animal Tissues", The Journal of Biological Chemistry, received for publication Aug. 23, 1956, vol. 226, p. 497-509.
Michael Stacey et al., "Differential effects in cells exposed to ultra-short, high intensity electric fields: cell survival, DNA damage, and cell cycle analysis", Mutation Research, Science Direct, Aug. 2003, vol. 542, pp. 65-75.
Ramanathan Ranjith Kumar et al., "Lipid extraction methods from microalgae: a comprehensive review" Frontiers in Energy Research, Jan. 8, 2015, vol. 2, Article 61, pp. 1-9.
Roberta Miglio et al., "Microalgae triacylglycerols content by FT-IR spectroscopy", J Appl Phycol, 2013, vol. 25, pp. 1621-1631.
Ronald G. Sosnowski et al., "Rapid determination of single base mismatch mutations in DNA hybrids by direct electric field control", Proceedings of the National Acadey of Sciences (PNAS), 1997, vol. 94, pp. 1119-1123.
Tim de Mooij et al. , "Antenna size reduction as a strategy to increase biomass productivity: a great potential not yet realized", Oct. 19, 2014, vol. 27, No. 3, p. 1063-1077, XP035496510.
Written Opinion dated Feb. 3, 2020 re: Application No. PCT/IB2019/060472, pp. 1-5, citing: Perin et al. "Generation of random mutants . . . ".

\* cited by examiner

*Primary Examiner* — Robert J Yamasaki
*Assistant Examiner* — Trevor Kane
(74) *Attorney, Agent, or Firm* — CANTOR COLBURN LLP

(57) ABSTRACT

A microalgal strain of the species *Nannochloropsis gaditana* is characterized by a mutation of an enzyme involved in the biosynthesis of chlorophyll that changes the physiology thereof with respect to the wild-type strain of the same species. In particular, with the mutation, microalgae are formed which, with respect to the wild-type strain of the same species, have a lower chlorophyll content and a reduced capacity to absorb visible radiation (light).
Further, a process for the production of lipids through the cultivation of the mutated *Nannochloropsis gaditana* strain and the lipids obtained can be used as synthesis intermediates, particularly in the so-called "green-chemistry" sector or in the production of biofuels.

Figure 1:
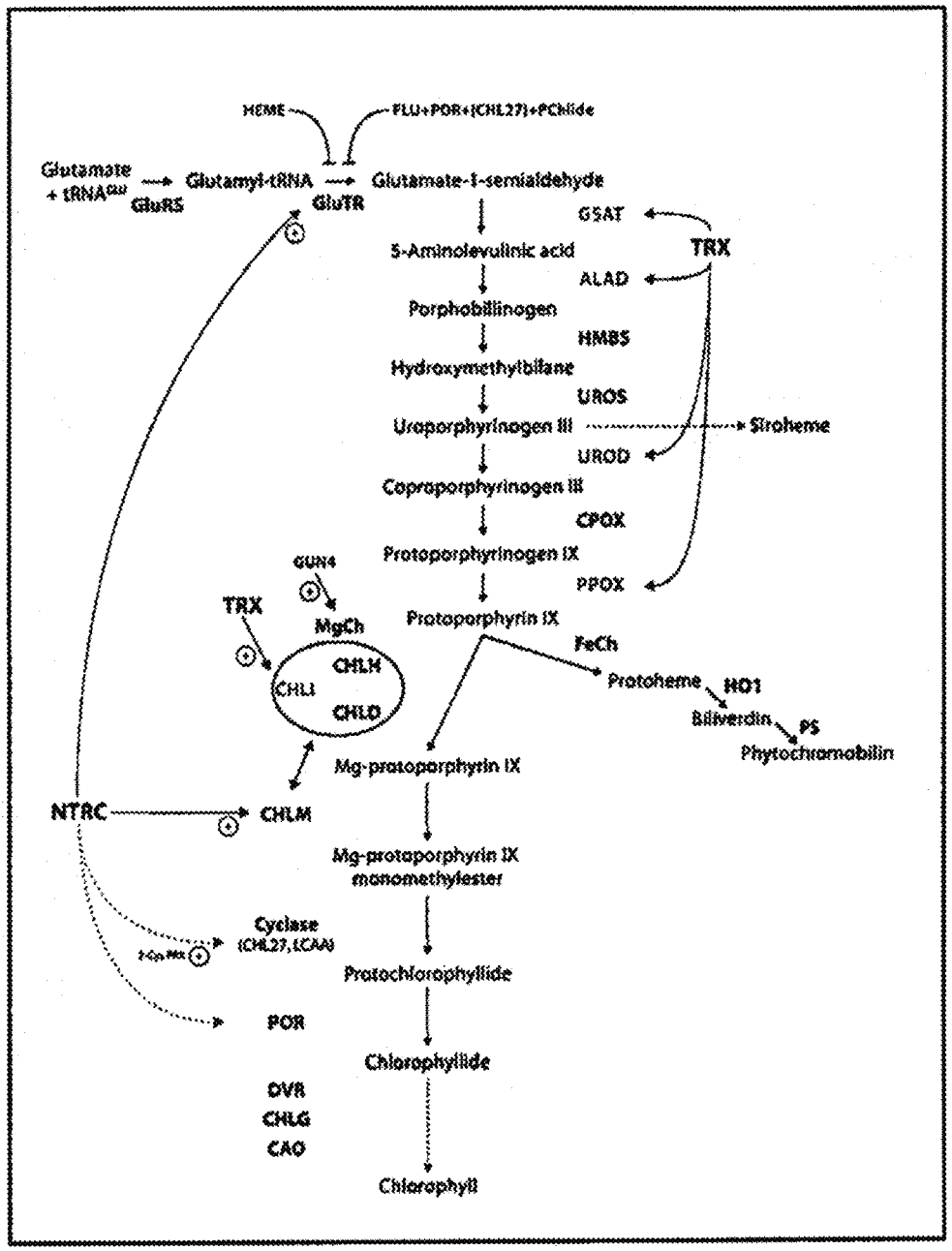

9 Claims, 4 Drawing Sheets
Specification includes a Sequence Listing.

FIGURE 4
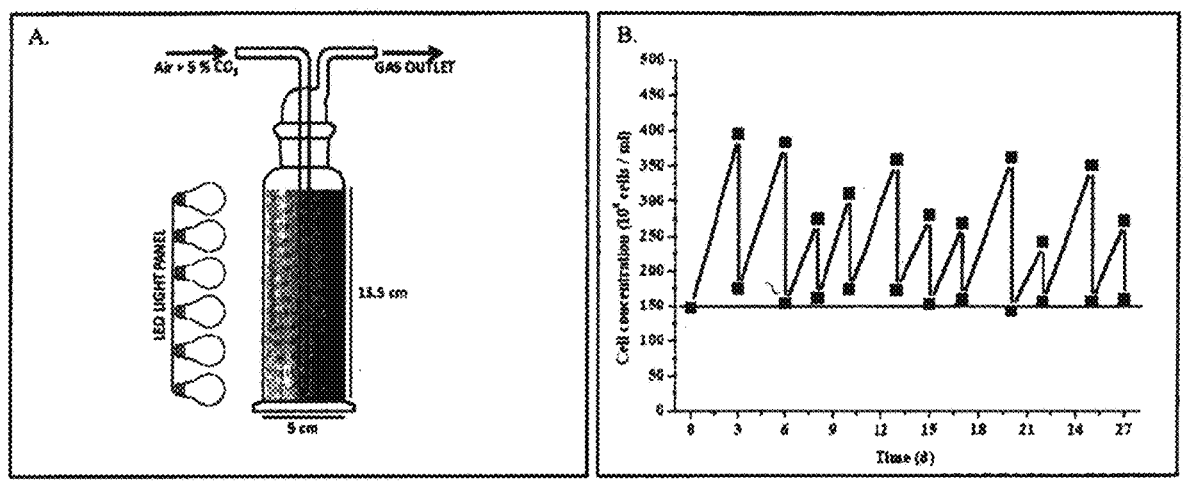
FIGURA 5
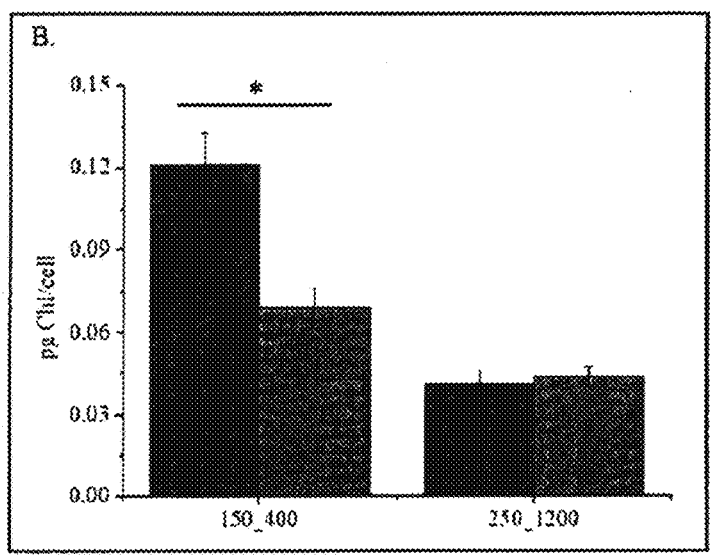

MICROALGAL STRAIN AND ITS USE FOR THE PRODUCTION OF LIPIDS

TECHNICAL FIELD

The present disclosure relates to a microalgal strain of the species *Nannochloropsis gaditana*.

More in particular, the present disclosure relates to a microalgal strain of the species *Nannochloropsis gaditana*, characterised by a mutation of an enzyme involved in the biosynthesis of chlorophyll that changes the physiology thereof with respect to the wild-type strain of the same species. In particular, thanks to said mutation, microalgae are obtained which, with respect to the wild-type strain of the same species, have a lower chlorophyll content and thus a reduced capacity to absorb visible radiation (light).

Said microalgal strain of the species *Nannochloropsis gaditana* is also characterised by higher yields of biomass and accumulated intracellular lipids that are similar or even higher than those of the wild-type strain.

Further, the present disclosure relates to a process for the production of lipids through the cultivation of said microalgal strain of the species *Nannochloropsis gaditana*.

The lipids thus obtained can be advantageously used as synthesis intermediates, particularly in the so-called "green chemistry" sector, or in the production of biofuels such as "biodiesel" or "green diesel", which can be used mixed with other fuels of mineral and plant origin for transportation, or as such.

The production of lipids through microbiological methods is proposed as an advantageous alternative to current production methods from renewable sources. With respect to the extraction of lipids from plants, microbiological processes are more cost effective as they are more easily scalable, require lower operating costs, and exploit the property of the microorganisms to quickly reproduce at low costs, at the expense of low cost substrates such as, for example, carbon dioxide ($CO_2$) present in combustion streams. Furthermore, they can be independent from climatic factors and do not compete with the agricultural exploitation of soil for food use.

Microalgae are particularly promising for this purpose. Microalgae represent an interesting alternative for the production of biofuels, as they can accumulate large amounts of lipids that can be converted into biofuels and can be grown in marginal areas using salt water and/or non-potable water. The accumulation of lipids, which is essential for conversion to bio-oil, in industrial scale growth, can be maximised through the limitation of nutrients (starvation), however the nutrient limitation condition blocks the growth of biomass, reducing industrial productivity.

BACKGROUND

Generally, said lipids are obtained by growing microalgae in aerobic conditions inside photobioreactors (optimal reactors for the growth of photosynthetic microorganisms, as they allow the growth of the aforesaid microorganisms in the presence of a source of natural or artificial light energy). The aerobic environment is generated by the development of $O_2$ after the biofixation of the molecules of carbon dioxide ($CO_2$) by the chlorophyll photosynthesis process. The microalgae of the *Nannochloropsis gaditana* species are grown using the culture medium called "F/2", with salinity equal to 32 g/l, which consists of a variant of the culture medium called "Medium F" processed by Guillard (1975) and whose composition differs from the original protocol as the concentration of the different components is halved with respect to the formulation of the culture medium originally processed by Guillard and Ryther (1962) for diatoms and other marine microalgae.

From the cultivation of said microalgae inside photobioreactors, a culture broth is obtained including a cellular biomass that is substantially constituted by microalgae, which must be recovered. Commonly, for the separation from the culture broth (aqueous phase rich in solubilised salts) of the cellular biomass, obtained at the end of the lipid production process, different techniques can be used, selected for example from: flocculation, flotation, spontaneous sedimentation, passage in hydrocyclones, centrifugation, filtration, microfiltration, ultrafiltration, filter pressing, sometimes continuously coupled with the photobioreactor in which said process is carried out. Subsequently, the lipids accumulated within the microalgae must be extracted and separated from the culture broth still present and from the cell debris, through appropriate cell membrane lysis or rupture techniques.

One of the main criticalities in relation to the production of lipids through microbiological methods relates to the fact that the volumetric productivity (i.e. the amount of lipids to be obtained per unit of volume of culture broth) is limited and, in general, is less than 10 g/L (it only reaches the level of 100 g/l after separation of the biomass culture broth). Therefore, the industrial application of these production processes envisages the use of high volumes of culture broth. These volumes of culture broth must be treated in large plants to recover the resulting cellular biomass and proceed with the extraction of lipids, which implies high investment and production costs.

For the purpose of guaranteeing a certain level of cost effectiveness of the lipid production process, the culture of microalgae must reach a high cell density, thus allowing the productivity of the process to be increased in order to minimise the volume of culture broth and the number of photobioreactors used.

However, the need to maximise the cell density implies the disadvantage of creating, inside the photobioreactor, an environment that is poorly irradiated by visible radiation or, better, irradiated with an amount of visible radiation suitable to promote the proliferation of microalgae only in the peripheral layers of the mass present in the photobioreactor, the closest layers to the source of light energy. For microalgae, as photosynthetic organisms, the availability of visible radiation is fundamental for growth. In fact, microalgae absorb radiation in the range of wavelengths ranging from 400 nm to 700 nm. However, in industrial systems the high concentrations reached by the cultures make the penetration of radiation inside the photobioreactor poor. This has a negative influence on the growth rate of the microalgae, with a consequent reduction of the production of lipids accumulated within them and a reduction of industrial production.

The problem of improving the productivity of microalgae cultures, connected with the amount of visible radiation was, for example, tackled in US patent application US2014295448A1. In fact, US2014295448A1 describes a method and a composition for reducing the dimensions of the antenna complex used in the photosynthesis process. This reduction takes place by reducing the expression of the TLA2 gene and leads to an improvement, in conditions of intense sunlight, of the effectiveness of the solar conversion and the photosynthetic productivity of the mutated microalgae.

Also the article by Perin et al., "Generation of random mutants to improve light-use efficiency of *Nannochloropsis*

*gaditana* cultures for biofuel production", Biotechnol Biofuels (2015) 8:161 faces the problem of improving the productivity of the microalgae cultures, connected with the amount of visible radiation available. For that purpose, some mutated microalgal strains are described, which have different phenotypes provided with alterations affecting the photosynthetic apparatus.

The production of lipids from renewable sources, that can be used for making synthesis intermediates in the so-called "green-chemistry" sector and as intermediates for the production of so-called "advanced nature biofuels", i.e. not in competition with crops for food use and with minimal impact on soil consumption, is still of great interest. The study of new microalgae able to produce the aforesaid lipids with good yields and to guarantee high industrial productivity is therefore of great interest.

SUMMARY

The Applicant therefore set out to solve the problem of identifying a microalga able to guarantee a high growth rate of the culture broth inside the photobioreactor and to produce lipids with a good yield.

The Applicant has now identified a microalgal strain that can solve such problem and others that will be better illustrated below.

In particular, the disclosure relates to a microalgal strain of the *Nannochloropsis gaditana* species deposited, in accordance with the Budapest Treaty, on 3 Oct. 2018 at the Culture Collection of Algae and Protozoa (CCAP), Oban, Argyll (Scotland, United Kingdom), access number CCAP 849/21, characterised by mutations of an enzyme involved in the biosynthesis of chlorophyll, which modifies the physiology with respect to the wild-type strain of the same species. In particular, thanks to said mutation, microalgae are formed which, with respect to the wild-type strain of the same species, have a lower chlorophyll content and a reduced capacity to absorb visible radiation. Further, said microalgal strain is characterised by high yields of biomass and intracellular lipid accumulation that are similar or even higher than that of the wild-type strain.

*Nannochloropsis gaditana* CCAP 849/21 is a marine microalga having spherical or slightly oval-shaped cells 2-4 μm in diameter. It belongs to the *Nannochloropsis* genus, included in the Eustigmatophyceae class within Heterokonta, a group that also comprises diatoms and brown algae. Table 1 shows the taxonomic rank of *Nannochloropsis gaditana* CCAP 849/21:

TABLE 1 taxonomic rank of *Nannochloropsis gaditana* CCAP849/21

| | |
|---|---|
| Domain | Eukaryota |
| Kingdom | Chromista |
| Subkingdom | Chromalveolata |
| Phylum | Heterokonta(Stramenopiles) |
| Class | Eustigmatophyceae |
| Order | Eustigmatales |
| Family | Eustigmataceae |
| Genus | *Nannochloropsis* |
| Species | *Nannochloropsis gaditana* CCAP 849/21 |

*Nannochloropsis gaditana* CCAP 849/21 is a single-cell microorganism on whose cell wall there is the biopolymer algaenan. This microorganism contains a single chloroplast, containing chlorophyll, while the main accessory pigments are esters of violaxanthin and vaucheraxanthin. It has a specific maximum growth rate ranging from 0.56 days$^{-1}$ to 1 day$^{-1}$, at the temperature of 23° C.

A further aspect of the present disclosure relates to a process for the production of lipids through the cultivation of said microalgal strain of the species *Nannochloropsis gaditana* CCAP 849/21.

The chlorophyll present inside the grains of the chloroplasts of the microalga is the main pigment involved in the absorption of visible radiation. The isolation of microalgal strains with a reduced chlorophyll content can therefore be advantageous for increasing the penetration of visible radiation inside the photobioreactors in which the microalgae are grown and thus increase the growth rate of the microalgae themselves, with the consequent increase in the production of lipids accumulated inside and the increase in industrial productivity.

In the present description and the following claims, the definitions of the numeric ranges always comprise the extremes and individual values within the range itself.

In the present description and the following claims, the term "biodiesel" means a fuel for diesel engines comprising alkyl esters (for example, methyl, propyl or ethyl) of long chain fatty acids deriving from biological sources.

In the present description and the following claims, the term "green diesel" means a fuel for diesel engines comprising hydrogenation or deoxygenation products of lipids deriving from biological sources.

In the present description and the following claims, the expressions "cultivation" and "culture" indicate the processes through which the cells of a microorganism grow and reproduce in human controlled conditions. The processes defined through the above expressions comprise the "culture" of the microalga, realised in some embodiments of the present disclosure.

In the present description and the following claims, the expression "culture medium" means a liquid, or a gel, provided to support the growth of the microalga cells. The culture medium can be of a defined composition (for example, "F/2" medium, etc.) or may derive from the treatment of non-selected sources such as, for example, waste water, sea water, organic waste obtained from processing plants, market waste, or hydrolysed lignocellulosic material.

In the present description and the following claims, the expressions "carbon source", "nitrogen source", "sulfur source" and "phosphorus source" mean organic or inorganic substances, or combinations thereof, containing carbon, nitrogen, sulfur (for example, sulfates) and/or phosphorus (for example, phosphates), present in the culture medium and that a microalga can metabolise for deriving energy.

In the present description and the following claims, the term "biomass" means the assembly of cells produced during the process for the production of lipids according to the present disclosure or in other culture methods.

Further features and advantages of the present disclosure will be apparent from the following detailed description.

Therefore, a first subject matter of the present disclosure is a microalgal strain of the *Nannochloropsis gaditana* species deposited, in accordance with the Budapest Treaty, on 3 Oct. 2018 at the Culture Collection of Algae and Protozoa (CCAP), Oban, Argyll (Scotland, United Kingdom), having access number CCAP 849/21.

DETAILED DESCRIPTION OF THE DRAWINGS

According to the present disclosure, the chlorophyll content present inside the chloroplasts of *Nannochloropsis* gaditana CCAP 849/21 is reduced because of the induction of a mutation of the gene codifying uroporphyrinogen decarboxylase (UROD), which codifies for an enzyme involved in the biosynthesis of tetrapyrroles, whose final products include chlorophyll (FIG. 1 shows a schematic representation of the biosynthetic pathway of the tetrapyrroles). This mutation causes an alteration of the UROD gene expression.

Advantageously, the mutation of this gene leads to a reduction of the chlorophyll content, but without causing any alterations to the composition and functionality of the photosynthetic apparatus, which comprises enzymes, proteins and molecules responsible for the sequence of stages necessary: to capture visible radiation (antenna complex), to the transformation of radiation into redox potential (reaction centre), to the translocation of redox potential (quinone and soluble cytochrome cycle), and finally to the transmembrane translocation of protons (cytochrome bc1). In fact, this mutation does not cause a reduction of the expression of the proteins of the antenna complex appointed to collect the visible radiation, which could have negative consequences on the survival of the microalga, nor does it affect the capacity of the microalga to adapt its photosynthetic apparatus to different light intensities (phenomenon known as "acclimatisation").

The reduction of the UROD gene expression, a key gene in the biosynthesis of chlorophyll, therefore allows the production and accumulation of chlorophyll within *Nannochloropsis gaditana* CCAP 849/21 to be reduced, without damaging the photosynthetic capacity of the microalga itself. As chlorophyll is the main pigment appointed to absorb visible radiation, the use inside photobioreactors of microalga provided with a reduced chlorophyll content allows improved penetration of visible radiation inside the photobioreactor, with a consequent increase in the growth rate of the microalgae, an increase in the overall production of the lipids accumulated within the microalgae and an increase in industrial production.

Advantageously, the reduction of the level of expression of the UROD gene does not display any side effects on the growth and capacity of the microalga to adapt to high exposure to visible radiation because, unlike what can happen by modifying the proteins of the antenna complex, this mutation does not affect the photoprotection mechanisms. In fact, *Nannochloropsis gaditana* CCAP 849/21 shows that it can adapt to any conditions of excess visible radiation without suffering any damage.

Preferably, the mutation characterising *Nannochloropsis gaditana* CCAP 849/21, according to the present disclosure, is obtained through a mutagenesis process, known to a person skilled in the art such as for example through a high voltage electroporation process, the aim of which is to induce random punctiform mutations within the genome of the microalga. Processes of this type are described in Sosnowski, Ronald G. et al., "Rapid determination of single base mismatch mutations in DNA hybrids by direct electric field control", Proc. Natl. Acad. Sci. 94:1119-1123 (1997) and in Stacey Michael et al., "Differential effects in cells exposed to ultra-short, high intensity electric fields: cell survival, DNA damage, and cell cycle analysis", Mutation Research 542: 65-75 (2003).

Once the electroporation process has been carried out, the selection of the microalga strain containing the mutation of interest (the one affecting the UROD gene) is preferably carried out by verifying the correct formation of the membrane pores during the electroporation process. For that purpose, an exogenous DNA providing the characteristic of resistance to the Zeocin antibiotic is added to the culture broth of the microalgae. It is known that if the electroporation process takes place correctly and pores are formed on the cell membrane, the exogenous DNA can penetrate into the cell, giving the latter the characteristics dictated by the exogenous DNA, a characteristic not present in cells in which the formation of pores did not occur. This discriminant allows the strains to be selected in which the electroporation process has produced the expected results (formation of pores and inclusion of the exogenous DNA). In fact, by adding a certain amount of the antibiotic Zeocin to the culture medium of the microalgae previously subjected to electroporation, only the microalgae provided with exogenous DNA can survive, thus allowing the strains in which the electroporation took place successfully to be selected.

As is known, since the formation of membrane pores only takes place when the electric discharge of the electroporation crosses the cell, it is important to carry out this type of selection in order to identify the microalgal strains that have undergone the mutation process caused by the radiation.

However, as the high voltage electroporation process induces random point mutations inside the genome of the microalga, it is important to isolate and select the microalgal strains characterised by the phenotype of interest, i.e. a reduced chlorophyll content. More details on the isolation and selection process of the microalgal strains expressing a reduced chlorophyll content can be found in the article previously mentioned in the name of Perin et al., Biotechnol Biofuels (2015) 8:161.

After identifying the microalgal strains expressing a reduced chlorophyll content, through gene sequencing techniques known to a person skilled in the art, it was possible to identify the mutations responsible for the phenotype. At this point the Applicant found that the mutation on the UROD gene is among the different mutations identified causing an alteration of the chlorophyll concentration level, the most advantageous one.

Further subject matter of the present disclosure is a process for the production of lipids comprising:
cultivating a *Nannochloropsis gaditana* CCAP 849/21 strain in a culture medium, under presence of visible radiation;
subjecting said culture to separation, obtaining an aqueous biomass suspension of *Nannochloropsis gaditana* CCAP 849/21 comprising intracellular lipids and an aqueous phase;
extracting the intracellular lipids accumulated inside *Nannochloropsis gaditana* CCAP 849/21.

Said cultivation can, preferably, take place inside a photobioreactor.

In accordance with a preferred embodiment of the present disclosure, said process can be carried out at a temperature ranging from 10° C. to 40° C., preferably ranging from 20° C. to 35° C.

In accordance with a preferred embodiment of the present disclosure, said process can be carried out in "fed-batch" or "continuous" mode.

In accordance with a preferred embodiment of the present disclosure, said process can be carried out in aerobic conditions.

Said aerobic conditions can be implemented, for example, by insufflating sterile air into the culture device and through variable agitation, said agitation depending on the type of culture device used.

In accordance with a preferred embodiment of the present disclosure, said process can be carried out at a pH ranging from 4.5 to 9.5, preferably ranging from 7.0 to 8.5, even more preferably ranging from 7.5 to 8.0. For the purpose of maintaining the pH in the desired ranges, an aqueous solution can be added to the culture medium of at least one base, selected for example from: sodium hydroxide (NaOH), potassium hydroxide (KOH), calcium dihydroxide [Ca(OH)$_2$], magnesium hydroxide [Mg(OH)$_2$], or mixtures thereof, preferably potassium hydroxide (KOH), or an aqueous solution of at least one acid selected, for example, from: phosphoric acid (H$_3$PO$_4$), sulphuric acid (H$_2$SO$_4$), hydrochloric acid (HCl), or mixtures thereof, preferably sulphuric acid (H$_2$SO$_4$), in an amount such as to obtain the desired pH.

In accordance with a preferred embodiment of the present disclosure, said process can be carried out starting from an inoculum in an amount ranging from 0.1% to 10% (vol/vol) of the total volume of culture medium, obtained from a previous culture of said *Nannochloropsis gaditana* strain CCAP 849/21, according to the present disclosure, carried out in the same culture medium for a time ranging from 6 hours to 72 hours.

Said previous culture can in turn be inoculated by a former culture, or can be inoculated starting from a sample of said strain CCAP 849/21, maintained at −80° C., as such or in suspension comprising 5% (vol/vol) ethylene glycol+5% (vol/vol) DMSO+10% L-Proline (vol/vol).

In accordance with a preferred embodiment of the present disclosure, said process can be carried out in an F/2 culture medium preferably enriched with sea salt, Tris-HCl, Guillard (F/2) marine water enrichment solution and nitrogen.

In accordance with a preferred embodiment of the present disclosure, said process, after a time ranging from 15 hours to 175 hours, after inoculation, can be further carried out in "fed-batch" or "continuous" mode, without time limits, by adding at least one further source of nitrogen, selected for example from: sodium nitrate, potassium nitrate, ammonium sulfate, ammonium carbonate or bicarbonate, ammonium chloride, urea, in an amount such as to add to the culture broth a total amount of nitrogen ranging from 0.02 g/l to 5 g/1, preferably ranging from 0.2 g/l to 5 g/1.

During the culture, the cell growth rate can be evaluated through spectrophotometric methods such as, for example, through turbidity or optical density (OD) analysis, of a sample of culture broth at 750 nm (OD$_{750}$), through counting the cells, or through determination of the dry weight according to methods known to a person skilled in the art.

According to the process of the disclosure, the step of subjecting the culture to separation, obtaining an aqueous solution of biomass of *Nannochloropsis gaditana* CCAP 849/21 comprising intracellular lipids and an aqueous phase is preferably carried out through techniques that are known in the state of the art selected, for example, from: flocculation, flotation, filtration, filter pressing, microfiltration, ultrafiltration, centrifugation or combinations thereof; preferably through centrifugation. Preferably, said centrifugation can be carried out for a time ranging from 5 minutes to 30 minutes, preferably ranging from 15 minutes to 25 minutes, at a rotation speed ranging from 3000 rpm to 9000 rpm, preferably ranging from 4000 rpm to 8000 rpm. It is to be noted that the operating conditions indicated for centrifugation relate to a process carried out on laboratory scale: in the case of an industrial process, in which generally continuous centrifugation is used, a person skilled in the art will be able to adapt said operating conditions.

The concentration of cellular biomass obtained can be measured in grams per litre of culture broth, determining the dry weight of the cells of microalga of a sample of culture broth of a known volume taken at pre-set intervals and at the end of said process. In particular, "dry weight" of cellular biomass means the weight of the cells contained in a known volume of culture broth, determined by weighing the aforesaid cells after removing all the water content through a heat treatment in a ventilated oven at 75° C. until constant weight (about 24 hours) and separating the salinity contribution of the culture medium through filtration and washing of the biomass or through determination of ash.

For the purpose of extracting the intracellular lipids accumulated inside *Nannochloropsis gaditana* CCAP 849/21, the *Nannochloropsis gaditana* CCAP 849/21 biomass can be subjected to cellular lysis according to processes known in the state of the art and described, for example, in international patent application WO 2014/102254 including, for example, a heat treatment in a pressurised reactor, a heat treatment in the presence of acid, such as, for example, sulphuric acid, hydrochloric acid, phosphoric acid or mixtures thereof, a mechanical treatment with homogenizer, a treatment with microwaves or with steam ("steam explosion").

At the end of said cell lysis, the lipids can be recovered from the suspension obtained, through extraction with polar or non-polar organic solvents, according to processes known in the state of the art and described, for example, in international patent application WO 2014/102254. Another example of prior art describing methods for extracting lipids from wet or dry cellular biomass is the document "Lipid extraction methods from microalgae: a comprehensive review" Ramanathan Ranjith Kumar et al., Frontiers in Energy Research 2015, Vol. 2, article 61, 1-9. Further extraction methods comprise the use of supercritical gases, ionic liquids or "deep eutectic solvents" (DES) as described, for example, in "Deep Eutectic Solvents (DESs) and Their Applications", Emma L. Smith et al., Chem. Rev. 2014, 114, 11060-11082.

The production of lipids by microalgae at the end of the process according to the present disclosure can be measured with colorimetric methods known in the state of the art, for example with Nile Red dye or with sulpho-phospho vanilline using the kit "Total lipids—sulpho-phospho vanilline" sold by Spinreact S.A.U., Ctra. Santa Coloma, 7 E-17176 St. Esteve d'en Bas (GI), Spain; or through spectrophotometric methods such as, for example, Fourier Transform Infrared Spectroscopy (FTIR) as described in "Microalgae triacylglycerols content by FTIR spectroscopy", Roberta Miglio et al., J Appl Phycol (2013) 25:1621-1631.

Further, the amount of lipids produced can be determined with gravimetric methods from the fraction extracted with mixtures of organic solvents, for example with chloroform:methanol 2:1, vol/vol as described in Folch J. et al, The Journal of Biological Chemistry, vol. 226, pag. 497-509 (1957); or extracted with n-hexane:isopropanol 3:2 vol/vol as described in Hara A. et al, Analytical Biochemistry, Vol. 90, pag. 420-426 (1978), from samples of freeze-dried biomass.

It is to be noted that, operating by the process according to the disclosure, the strain of the species *Nannochloropsis gaditana* CCAP 849/21, with respect to the wild-type strain of the same species, allows an increase in productivity of up to 25% and a corresponding increase in the lipid titer to be obtained.

The lipid fraction was analysed through chromatographic techniques, for example gas chromatography or high performance liquid chromatography (HPLC) according to processes known in the prior art.

Through said analytical methods it was detected that the lipids accumulated in the microalgae cells, both of the mutated strain and of the wild-type strain, are 90% represented by triglycerides, preferably esters of glycerol with fatty acids having 8 to 24 carbon atoms, such as, for example, palmitic acid, stearic acid, oleic acid and α-linolenic acid.

Other lipids that can be present are, for example: phospholipids, monoglycerides, diglycerides, free fatty acids, or mixtures thereof.

The lipids obtained according to the process of the present disclosure can be subjected to hydrogenation/deoxygenation in the presence of hydrogen and at least one catalyst in order to produce "green diesel". Hydrogenation/deoxygenation processes are known in the prior art and are described, for example, in EP1728844. Further, the aforesaid lipids can be subjected to transesterification in the presence of at least one alcohol having 1 to 4 carbon atoms, preferably methanol or ethanol, and at least one acidic or basic catalyst, in order to produce glycerol and alkyl esters, in particular methyl esters or ethyl esters. Alternatively, the aforesaid lipids can be advantageously used as synthesis intermediates, particularly in the so-called "green chemistry" sector.

For the purpose of putting the present disclosure into practice and illustrating it more clearly, below are some non-limiting examples.

Example 1 (Obtaining the CCAP 849/21 Strain of the *Nannochloropsis gaditana* Species)

An embodiment is described below of the method of obtaining the microalgal strain of the *Nannochloropsis gaditana* species deposited, in accordance with the Budapest Treaty, on 3 Oct. 2018 at the Culture Collection of Algae and Protozoa (CCAP), Oban, Argyll (Scotland, United Kingdom), access number CCAP 849/21. In this example, mutagenesis was obtained through electromagnetic radiation.

For that purpose, $7*10^6$ cells/ml of a wild-type strain of microalga of the *Nannochloropsis gaditana* species CCAP 849/5 were grown for 5 days in Drechsel bottles having a diameter of 5 cm, working volume of 250 ml and subjected to bubbling with air enriched with 5% (v/v) of $CO_2$. The culture medium used was F/2 with sea salt (32 g/l, Sigma-Aldrich®), 40 mM Tris-HCl (pH 8) and enriched Guillard sea water solution (F/2) (Sigma-Aldrich®) additioned with nitrogen (final concentration 12 mM $NaNO_3$). In the growth chamber, the intensity of the visible radiation (fundamental for the growth of the microalgae) was set to illumination of 120 µmol photons $m^2$ $s^{-1}$ at 22±1° C. To induce the mutation, $5*10^8$ cells of *N gaditana* were washed four times with sorbitol 375 mM at 4° C. and re-suspended in 100 µl of cold sorbitol 375 mM. Subsequently, the cells were subjected to an electroporation process in 2 mm cuvettes using the set for electroporation Electro Cell Manipulator ECM630 BTX™ (500 Ω, 50 µF and 2400 V). Subsequently, the cells were re-suspended in 10 ml of F/2 medium and left for 48 hours at 22±1° C. under stirring and 20 µmol photons $m^{-2}$ $s^{-1}$ before being plated. The mutation of the microalga genome was induced through electroporation of the cells using a high voltage in order to induce random punctiform mutations. In order to verify the correctness of the electroporation process, exogenous DNA was added, as a selection marker, for resistance to the antibiotic Zeocin. In this way, by selecting the colonies resistant to the antibiotic Zeocin, it was possible to guarantee that these colonies had correctly undergone the electroporation process and had therefore developed some random punctiform mutations within their endogenous DNA.

Example 2 (Analysis of the CCAP 849/21 Strain of the *Nannochloropsis Gaditana* Species)

Mutation of the UROD Gene

Figure 2:
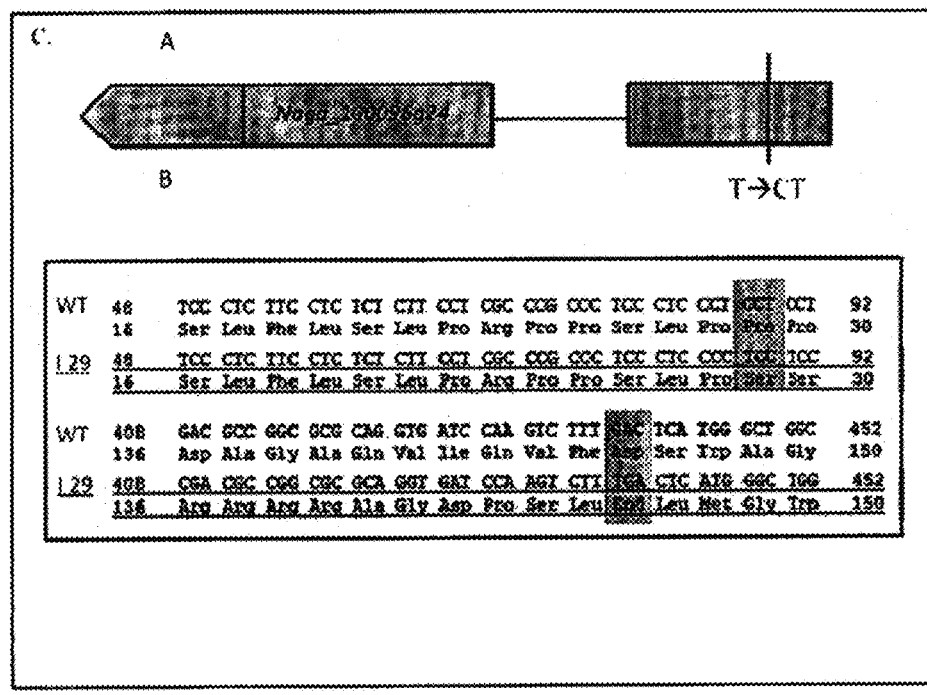

*Nannochloropsis gaditana* CCAP 849/21 is characterised by a mutation on the UROD gene. This mutation is a punctiform mutation, which led to the formation of a premature stop codon and therefore to the suppression of the expression of the mutant allele of the gene (FIG. 2).

FIG. 2A represents a schematic structure of part of the UROD gene in which the punctiform mutation is indicated: the insertion of a cytosine, upstream of a thymine, within the first exon of the gene. FIG. 2B instead represents the comparison by the nucleotide sequence, with related translation codons, of the wild-type gene UROD ("WT") with respect to the mutated gene ("I 29"), the sequence of which are reported in SEQ ID NO:1 and SEQ ID NO:2. In this figure it is possible to see how the mutation, the insertion of a cytosine upstream of the thymine in position 86 determines, further downstream, the formation of a stop codon.

Effects of the Mutation of the UROD Gene

Figure 3:
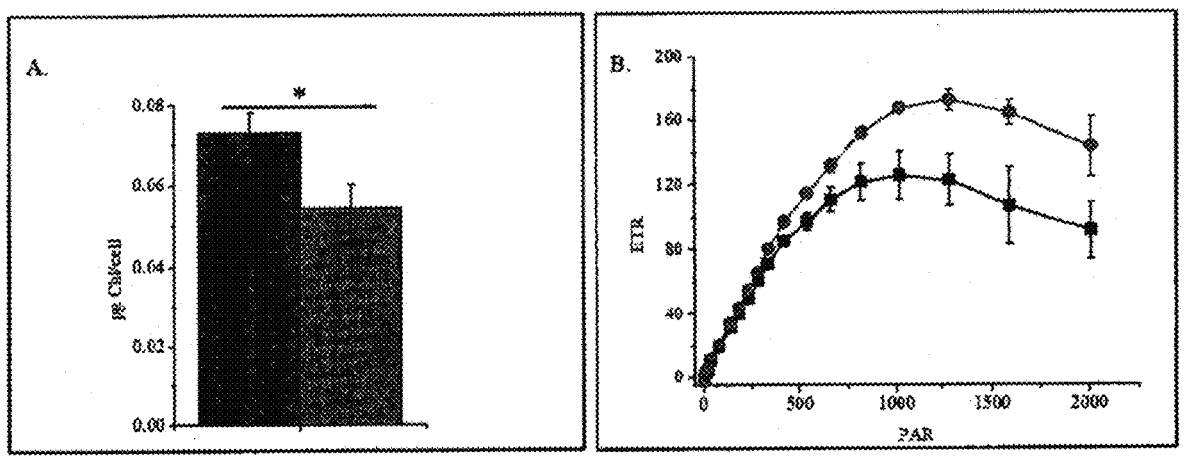

As can be seen from the graphs in FIG. 3, *Nannochloropsis gaditana* CCAP 849/21 has shown a 20% reduction of the chlorophyll content with respect to the wild-type strain of the same species, which accompanies greater photosynthetic electron transport, an indicator of a greater ability to use light energy for photosynthesis.

In fact, FIG. 3A shows a graph representing the chlorophyll content of microalgae of the wild-type strain (left column) and the chlorophyll content of *Nannochloropsis gaditana* CCAP 849/21 (right column). The statistically significant difference between the two strains is identified with an asterisk (one-way ANOVA, p-value <0.05). Instead, FIG. 3B shows a graph representing the saturation kinetics of the ETR ("Electron Transfer Rate"), determined through PAM ("Pulse Amplitude Modulation") fluorimeter at increasing light intensities over time. The dark grey shows the wild-type strain whereas the light grey shows *Nannochloropsis gaditana* CCAP 849/21.

Productivity Evaluation

The productivity of *Nannochloropsis gaditana* CCAP 849/21 was also evaluated when grown inside an experimental photobioreactor. The aim of this study was that of verifying the effect of the mutation of the UROD gene with reference to the production of biomass over time, when the culture reaches a high optical density level and the penetration of the visible radiation becomes limiting. To simulate industrial conditions a fed-batch reactor was used in which, every two days, the culture was diluted until an initial pre-established concentration was reached. The productivity was evaluated in terms of biomass (FIG. 4).

FIG. 4A schematically represents the experimental photobioreactor used: it comprises a Drechsel bottle having a diameter of 5 cm, a tube for insufflating a mixture of air and 5% $CO_2$ and a set of LED lamps for providing the visible radiation. FIG. 4B shows a graph representing the concentration of the biomass, contained in the photobioreactor, over time. The initial concentration of the biomass was set to $150 \times 10^6$ cells/ml. By simulating the industrial conditions of a fed-batch reactor, the culture was brought back to the initial concentration every two days through dilution with fresh culture medium.

In order to evaluate the productivity of *Nannochloropsis gaditana* CCAP 849/21 with respect to the wild-type strain, expressed in terms of concentration of biomass inside the photobioreactor, two culture conditions were considered:
1) initial concentration of $150 \times 10^6$ cells/ml; light intensity 400 µmol photons $m^{-2}s^{-1}$;
2) initial concentration of $250 \times 10^6$ cells/ml; light intensity 1200 µmol photons $m^{-2}s^{-1}$.

The results of the cultures carried out with these two conditions are shown in Table 2.

TABLE 2

| | Dry weight of the biomass (g/l/day) | |
|---|---|---|
| | Culture condition 1 | Culture condition 2 |
| Wild-type strain (n = 37) | 0.33 ± 0.05 | 0.48 ± 0.11 |
| Nannochloropsis gaditana CCAP 849/21 (n = 10) | 0.39 ± 0.05** | 0.47 ± 0.12 |

**statistically significant difference between the wild-type strain and *Nannochloropsis gaditana* CCAP 849/21 (one-way ANOVA, p-value < 0.05).

As can be seen in Table 2, *Nannochloropsis gaditana* CCAP 849/21 demonstrated higher productivity with respect to the wild-type strain in the condition of culture 1, where it manages to accumulate over 14% more biomass with respect to the wild-type strain whereas, in culture condition 2, it does not demonstrate any significant differences with respect to the wild-type strain.

As the condition of culture 2 envisages a high level of light intensity (1200 μmol photons $m^{-2}s^{-1}$), this latter datum demonstrates that the mutation of the UROD gene of *Nannochloropsis gaditana* CCAP 849/21 does not make the strain photosensitive. Also in high light intensity conditions *Nannochloropsis gaditana* CCAP 849/21 in fact demonstrates equal productivity of biomass with respect to the wild-type strain.

For both strains, under the same culture conditions, the chlorophyll content was also evaluated (FIG. 5). In fact, FIG. 5 shows a graph expressing the concentration of chlorophyll, per microalga cell (pg Chl/cell), contained both in the wild-type strain (dark grey), and in *Nannochloropsis gaditana* CCAP 849/21 (light grey), when grown in the aforesaid culture conditions (culture condition 1, indicated in the graph as 150_400 and culture condition 2, indicated in the graph as 250_1200; the statistically significant differences were highlighted with an asterisk, one-way ANOVA, p-value <0.05). From FIG. 5 it is clear that, in culture condition 1, *Nannochloropsis gaditana* CCAP 849/21 demonstrates having a 43% lower chlorophyll concentration with respect to the wild-type strain; whereas in culture condition 2 the concentration of chlorophyll between the two strains is not significantly different.

The data that demonstrate the reduction of the chlorophyll concentration and the increased productivity of biomass of *Nannochloropsis gaditana* CCAP 849/21 when grown in the condition of culture 1, confirm the hypothesis that a reduced chlorophyll content is more advantageous in limited light conditions (such as in the condition of culture 1), as this reduced chlorophyll content guarantees greater diffusion of the limited visible radiation within the entire photobioreactor, also in high cell density conditions, thus guaranteeing a high level of productivity of biomass over time.

Example 3 [Non Photochemical Quenching (NPQ) and Productivity]

Figure 6:
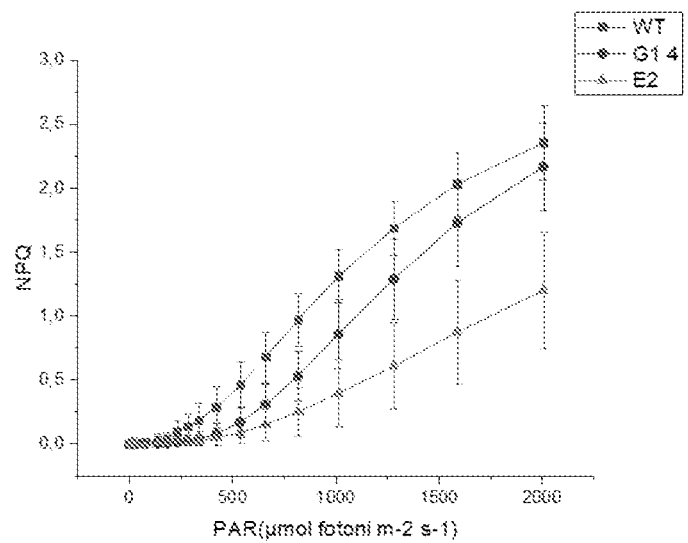

In order to evaluate the Non Photochemical Quenching (NPQ) of *Nannochloropsis gaditana* CCAP 849/21 with respect to the wild-type strain and to the mutant of *Nannochloropsis gaditana* E2 obtained as disclosed in the article of Perin et al., "Generation of random mutants to improve light-use efficiency of *Nannochloropsis gaditana* cultures for biofuels production, Biotechnol Biofuels" (2015) 8:161, above reported, the same were subjected to the following cultures conditions: initial concentration of $150 \times 10^6$ cells/ml; light intensity up to 2000 μmol photons $m^{-2}s^{-1}$ (FIG. 6). FIG. 6 clearly shows that the *Nannochloropsis gaditana* CCAP 849/21 (G14) reaches a NPQ activation comparable to the wild-type strain, while the mutant of *Nannochloropsis gaditana* E2 reaches a NPQ activation lower than both *Nannochloropsis gaditana* CCAP 849/21 (G14) and wild-type strain.

Figure 7:
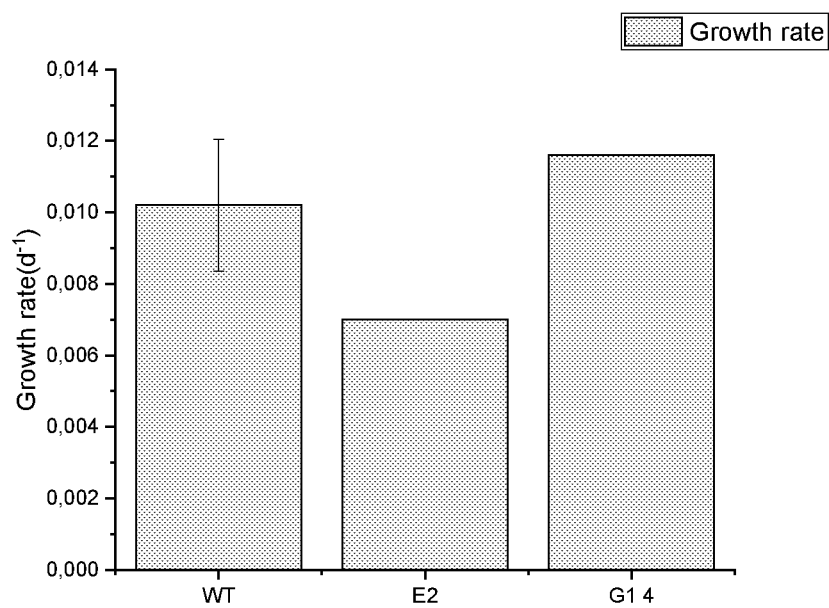

Moreover, the productivity of *Nannochloropsis gaditana* CCAP 849/21 with respect to the wild-type strain and to the mutant of *Nannochloropsis gaditana* E2 was evaluated under these culture conditions: initial concentration of $150 \times 10^6$ cells/ml; light intensity 500 μmol photons $m^{-2}s^{-1}$ (FIG. 7). FIG. 7 clearly shows that the *Nannochloropsis gaditana* CCAP 849/21 (G14) has a growth rate (expressed in $d^{-1}$) higher than the wild-type strain, while the mutant of *Nannochloropsis gaditana* E2 has a growth rate lower than both *Nannochloropsis gaditana* CCAP 849/21 (G14) and wild-type strain.

The invention claimed is:

1. A microalgal strain of *Nannochloropsis gaditana* species deposited, in accordance with Budapest Treaty, at the Culture Collection of Algae and Protozoa (CCAP), Oban, access number CCAP 849/21.

2. A process for the production of lipids, the process including the following steps:
 cultivating a *Nannochloropsis gaditana* CCAP 849/21 strain in a culture medium, under presence of visible radiation;
 subjecting said culture to separation, obtaining an aqueous biomass suspension of *Nannochloropsis gaditana* CCAP 849/21 comprising intracellular lipids and an aqueous phase; and
 extracting the intracellular lipids accumulated inside *Nannochloropsis gaditana* CCAP 849/21.

3. The process according to claim 2, wherein said process for the production of lipids is carried out:
 at a temperature ranging from 10° C. to 40° C.; and/or
 under aerobic conditions; and/or
 is carried out at a pH ranging from 4.5 to 9.5.

4. The process according to claim 2, wherein said process for the production of lipids is carried out starting from an inoculum in an amount ranging from 0.1% to 10% (vol/vol) of the culture medium total volume, obtained from a previous culture of said *Nannochloropsis gaditana* CCAP 849/21 strain, carried out in the same culture medium for a time ranging from 6 hours to 72 hours.

5. The process according to claim 2, wherein said process is carried out in a F/2 culture medium having sea salt, Tris-HCl, a Guillard (F/2) marine water enrichment solution, and nitrogen.

6. The process according to claim 2, wherein said process for the production of lipids is carried out in a discontinuous mode or in a continuous mode.

7. The process according to claim 6, wherein said process, after a time ranging from 15 hours to 175 hours after inoculation, is further carried out in the discontinuous mode or in the continuous mode, without time limit, adding at least one further source of nitrogen, in an amount such as adding to culture medium a nitrogen amount ranging from 0.02 g/l to 5 g/l.

8. The process according to claim 2, wherein the step of subjecting the culture to separation is carried out by techniques selected from: flocculation, flotation, filtration, filter pressing, microfiltration, ultrafiltration, centrifugation or combinations thereof.

9. The process according to claim 2, wherein the step of extracting the intracellular lipids is carried out by cellular lysis of *Nannochloropsis gaditana* CCAP 849/21 biomass.

* * * * *

SEQUENCE LISTING

<160> NUMBER OF SEQ ID NOS: 2

<210> SEQ ID NO 1
<211> LENGTH: 45
<212> TYPE: DNA
<213> ORGANISM: Nannochloropsis gaditana CCAP 849/21
<220> FEATURE:
<223> OTHER INFORMATION: location 48...92

<400> SEQUENCE: 1
tccctcttcc tctctcttcc tcgcccgccc tccctccct cctcc   45

<210> SEQ ID NO 2
<211> LENGTH: 45
<212> TYPE: DNA
<213> ORGANISM: Nannochloropsis gaditana CCAP 849/21
<220> FEATURE:
<223> OTHER INFORMATION: location 408...452

-continued

```
<400> SEQUENCE: 2
cgacgccggc gcgcaggtga tccaagtctt tgactcatgg gctgg          45
```